(12) United States Patent
Babaev et al.

(10) Patent No.: US 7,785,277 B2
(45) Date of Patent: Aug. 31, 2010

(54) REMOVABLE APPLICATOR NOZZLE FOR ULTRASOUND WOUND THERAPY DEVICE

(75) Inventors: Eilaz Babaev, Minnetonka, MN (US); Alan Van Houten, Carver, MN (US); Michael T. Peterson, Lakeville, MN (US); Greg Doten, Crystal, MN (US)

(73) Assignee: Celleration, Inc., Eden Prairie, MN (US)

( * ) Notice: Subject to any disclaimer, the term of this patent is extended or adjusted under 35 U.S.C. 154(b) by 0 days.

(21) Appl. No.: 11/473,934

(22) Filed: Jun. 23, 2006
(Under 37 CFR 1.47)

(65) Prior Publication Data

US 2007/0088245 A1    Apr. 19, 2007

Related U.S. Application Data

(63) Continuation-in-part of application No. 11/168,620, filed on Jun. 27, 2005.

(60) Provisional application No. 60/693,560, filed on Jun. 23, 2005.

(51) Int. Cl.
*A61H 1/00* (2006.01)

(52) U.S. Cl. .......................................... 601/2; 600/439

(58) Field of Classification Search ............... 222/4, 222/5, 80, 81, 165, 167, 181.2, 594, 598, 222/617; 251/208; 600/407, 408, 439, 489; 601/2–4; 604/20–22

See application file for complete search history.

(56) References Cited

U.S. PATENT DOCUMENTS 2,534,046 A * 12/1950 Mau ........................... 422/269

(Continued)

FOREIGN PATENT DOCUMENTS

EP    0 156 4009 A2    2/1985

(Continued)

OTHER PUBLICATIONS

Journal of Burn Care & Rehabilitation; vol. 21, No. 4; Jul./Aug. 2000 pp. 333-338.

(Continued)

*Primary Examiner*—Long V Le
*Assistant Examiner*—Saurel J Selkin
(74) *Attorney, Agent, or Firm*—Patterson, Thuente, Skaar & Christensen, P.A.

(57) ABSTRACT

A removable applicator nozzle for use in treating a wound is provided. The removable applicator nozzle includes a nozzle, a valve and a cup. The nozzle includes a proximal portion, a distal opening and a valve interface. The proximal portion of the nozzle is engagable with a portion of a transducer of an ultrasound wound therapy device. The distal opening of the nozzle allows at least a portion of a tip of the transducer to pass therethrough. The valve is engagable with the valve interface of the nozzle and the valve selectively allows fluid to flow therethrough. The cup includes an aperture and a puncturing device. The aperture is engagable with the valve and the puncturing device is able to puncture a bottle that is inserted on the cup. Fluid flows from the bottle, through the aperture and the valve and onto a tip of the transducer. The fluid is then moved to the distal opening of the nozzle by a vacuum effect.

59 Claims, 6 Drawing Sheets

U.S. PATENT DOCUMENTS

| | | | |
|---|---|---|---|
| 2,889,852 A * | 6/1959 | Dunlap | 137/625.19 |
| 3,207,181 A * | 9/1965 | Elizabeth | 137/625.31 |
| 3,243,122 A | 3/1966 | Snaper | |
| 3,275,059 A | 9/1966 | McCullough | |
| 3,392,916 A | 7/1968 | Engstrom et al. | |
| 3,504,887 A * | 4/1970 | Okerblom | 251/208 |
| 3,561,444 A | 2/1971 | Boucher | |
| 3,685,694 A * | 8/1972 | Ianelli | 222/82 |
| 3,765,606 A | 10/1973 | Moss et al. | |
| 3,860,173 A | 1/1975 | Sata | |
| 3,952,918 A | 4/1976 | Poitras | |
| 4,052,004 A | 10/1977 | Martin et al. | |
| 4,085,893 A | 4/1978 | Durley, III | |
| 4,153,201 A | 5/1979 | Berger et al. | |
| 4,251,031 A | 2/1981 | Martin et al. | |
| 4,271,705 A | 6/1981 | Crostack | |
| 4,294,407 A | 10/1981 | Reichl et al. | |
| 4,301,093 A | 11/1981 | Eck | |
| 4,301,968 A | 11/1981 | Berger et al. | |
| 4,309,989 A | 1/1982 | Fahim | |
| 4,319,155 A | 3/1982 | Nakai et al. | |
| 4,334,531 A | 6/1982 | Reichl et al. | |
| 4,352,459 A | 10/1982 | Berger et al. | |
| 4,414,202 A | 11/1983 | Silvetti | |
| 4,428,531 A | 1/1984 | Martin | |
| 4,466,571 A | 8/1984 | Muhlbauer | |
| 4,530,360 A | 7/1985 | Duarte | |
| 4,541,564 A | 9/1985 | Berger et al. | |
| 4,582,149 A * | 4/1986 | Slaughter, Jr. | 175/340 |
| 4,582,654 A | 4/1986 | Karnicky et al. | |
| 4,619,400 A | 10/1986 | Van Der Burgt | |
| 4,642,581 A | 2/1987 | Erickson | |
| 4,655,393 A | 4/1987 | Berger | |
| 4,659,014 A | 4/1987 | Soth et al. | |
| 4,679,551 A | 7/1987 | Anthony | |
| 4,726,523 A | 2/1988 | Kokubo et al. | |
| 4,726,525 A | 2/1988 | Yonekawa et al. | |
| 4,733,820 A | 3/1988 | Endo et al. | |
| 4,756,478 A | 7/1988 | Endo et al. | |
| 4,783,003 A | 11/1988 | Hirabayashi et al. | |
| 4,790,479 A | 12/1988 | Matsumoto et al. | |
| 4,793,339 A | 12/1988 | Matsumoto et al. | |
| 4,818,697 A | 4/1989 | Liboff et al. | |
| 4,850,534 A | 7/1989 | Takahashi et al. | |
| 4,877,989 A | 10/1989 | Drews et al. | |
| 4,905,671 A | 3/1990 | Senge et al. | |
| 4,930,700 A | 6/1990 | McKown | |
| 4,941,614 A | 7/1990 | Ilott | |
| 4,941,618 A | 7/1990 | Hildebrand et al. | |
| 4,961,885 A | 10/1990 | Avrahami et al. | |
| 4,982,730 A | 1/1991 | Lewis, Jr. | |
| 5,002,059 A | 3/1991 | Crowley et al. | |
| 5,013,241 A | 5/1991 | von Gutfeld et al. | |
| 5,040,537 A | 8/1991 | Katakura | |
| 5,063,922 A | 11/1991 | Hakkinen | |
| 5,076,266 A | 12/1991 | Babaev | |
| 5,104,042 A | 4/1992 | McKown | |
| 5,115,805 A | 5/1992 | Bommannan et al. | |
| 5,134,993 A | 8/1992 | van der Linden et al. | |
| 5,143,588 A | 9/1992 | Liboff et al. | |
| 5,163,433 A | 11/1992 | Kagawa et al. | |
| 5,172,692 A | 12/1992 | Kulow et al. | |
| 5,186,162 A | 2/1993 | Talish et al. | |
| 5,197,946 A | 3/1993 | Tachibana | |
| 5,211,160 A | 5/1993 | Talish et al. | |
| 5,231,975 A | 8/1993 | Bommannan et al. | |
| 5,259,384 A | 11/1993 | Kaufman et al. | |
| 5,269,291 A | 12/1993 | Carter | |
| 5,309,898 A | 5/1994 | Kaufman et al. | |
| 5,315,998 A | 5/1994 | Tachibana et al. | |
| 5,316,000 A | 5/1994 | Chapelon et al. | |
| 5,318,014 A | 6/1994 | Carter | |
| 5,323,769 A | 6/1994 | Bommannan et al. | |
| 5,324,255 A | 6/1994 | Passafaro et al. | |
| 5,345,940 A | 9/1994 | Seward et al. | |
| 5,347,998 A | 9/1994 | Hodson et al. | |
| 5,362,309 A | 11/1994 | Carter | |
| 5,374,266 A | 12/1994 | Kataoka et al. | |
| 5,380,411 A | 1/1995 | Schlief | |
| 5,393,296 A | 2/1995 | Rattner | |
| 5,437,606 A | 8/1995 | Tsukamoto | |
| 5,515,841 A | 5/1996 | Robertson et al. | |
| 5,515,842 A | 5/1996 | Ramseyer et al. | |
| 5,516,043 A | 5/1996 | Manna et al. | |
| 5,520,166 A | 5/1996 | Ritson et al. | |
| 5,520,612 A | 5/1996 | Winder et al. | |
| 5,527,350 A | 6/1996 | Grove et al. | |
| 5,529,572 A | 6/1996 | Spector | |
| 5,545,124 A | 8/1996 | Krause et al. | |
| 5,547,459 A | 8/1996 | Kaufman et al. | |
| 5,551,416 A | 9/1996 | Stimpson et al. | |
| 5,554,172 A | 9/1996 | Horner et al. | |
| 5,556,372 A | 9/1996 | Talish et al. | |
| 5,573,497 A | 11/1996 | Chapelon | |
| 5,616,140 A | 4/1997 | Prescott | |
| 5,618,275 A | 4/1997 | Bock | |
| 5,626,554 A | 5/1997 | Ryaby et al. | |
| 5,643,179 A | 7/1997 | Fujimoto | |
| 5,656,016 A | 8/1997 | Ogden | |
| 5,658,323 A | 8/1997 | Miller | |
| 5,688,224 A | 11/1997 | Forkey et al. | |
| 5,699,805 A | 12/1997 | Seward et al. | |
| 5,707,402 A | 1/1998 | Heim | |
| 5,707,403 A | 1/1998 | Grove et al. | |
| 5,730,705 A | 3/1998 | Talish et al. | |
| 5,735,811 A | 4/1998 | Brisken | |
| 5,743,863 A | 4/1998 | Chapelon | |
| 5,752,924 A | 5/1998 | Kaufman et al. | |
| 5,762,616 A | 6/1998 | Talish | |
| 5,785,972 A | 7/1998 | Tyler | |
| 5,835,678 A | 11/1998 | Li et al. | |
| 5,843,139 A | 12/1998 | Goedeke et al. | |
| 5,879,314 A | 3/1999 | Peterson et al. | |
| 5,879,364 A | 3/1999 | Bromfield et al. | |
| 5,882,302 A | 3/1999 | Driscoll, Jr. et al. | |
| 5,894,841 A | 4/1999 | Voges | |
| 5,904,659 A | 5/1999 | Duarte et al. | |
| 5,947,921 A | 9/1999 | Johnson et al. | |
| 5,960,792 A | 10/1999 | Lloyd et al. | |
| 5,989,245 A | 11/1999 | Prescott | |
| 6,001,069 A | 12/1999 | Tachibana et al. | |
| 6,014,970 A | 1/2000 | Ivri et al. | |
| 6,024,718 A | 2/2000 | Chen et al. | |
| 6,026,808 A | 2/2000 | Armer et al. | |
| 6,027,495 A | 2/2000 | Miller | |
| 6,041,253 A | 3/2000 | Kost et al. | |
| 6,061,597 A | 5/2000 | Rieman et al. | |
| 6,076,519 A | 6/2000 | Johnson | |
| 6,083,159 A | 7/2000 | Driscoll, Jr. et al. | |
| 6,095,141 A | 8/2000 | Armer et al. | |
| 6,098,620 A | 8/2000 | Lloyd et al. | |
| 6,102,298 A | 8/2000 | Bush et al. | |
| 6,106,547 A | 8/2000 | Huei-Jung | |
| 6,113,558 A | 9/2000 | Rosenschein et al. | |
| 6,113,570 A | 9/2000 | Siegel et al. | |
| RE36,939 E | 10/2000 | Tachibana et al. | |
| 6,158,388 A * | 12/2000 | Wenstrand | 119/464 |
| 6,158,431 A | 12/2000 | Poole | |
| 6,161,536 A | 12/2000 | Redmon et al. | |
| 6,176,839 B1 | 1/2001 | DeLuis et al. | |
| 6,186,963 B1 | 2/2001 | Schwarze et al. | |
| 6,190,315 B1 | 2/2001 | Kost et al. | |
| 6,190,336 B1 | 2/2001 | Duarte et al. | |
| 6,206,842 B1 | 3/2001 | Tu et al. | |

| | | | |
|---|---|---|---|
| 6,206,843 B1 | 3/2001 | Iger et al. | |
| 6,231,528 B1 | 5/2001 | Kaufman et al. | |
| 6,234,990 B1 | 5/2001 | Rowe et al. | |
| 6,251,099 B1 | 6/2001 | Kollias et al. | |
| 6,254,294 B1* | 7/2001 | Muhar | 401/26 |
| 6,273,864 B1 | 8/2001 | Duarte et al. | |
| 6,311,573 B1 | 11/2001 | Bhardwaj | |
| 6,321,109 B2 | 11/2001 | Ben-Haim et al. | |
| 6,322,527 B1 | 11/2001 | Talish | |
| 6,325,769 B1 | 12/2001 | Klopotek | |
| 6,450,417 B1 | 9/2002 | Gipson et al. | |
| 6,478,754 B1 | 11/2002 | Babaev | |
| 6,500,133 B2 | 12/2002 | Martin et al. | |
| 6,533,484 B1 | 3/2003 | Osei et al. | |
| 6,533,803 B2 | 3/2003 | Babaev | |
| 6,569,099 B1* | 5/2003 | Babaev | 600/439 |
| 6,583,071 B1 | 6/2003 | Weidman et al. | |
| 6,601,581 B1 | 8/2003 | Babaev | |
| 6,623,444 B2 | 9/2003 | Babaev | |
| 6,659,365 B2 | 12/2003 | Gipson et al. | |
| 6,663,554 B2 | 12/2003 | Babaev | |
| 6,666,431 B2* | 12/2003 | McCusker | 251/129.15 |
| 6,723,064 B2 | 4/2004 | Babaev | |
| 6,732,744 B2 | 5/2004 | Olshavsky et al. | |
| 6,761,729 B2 | 7/2004 | Babaev | |
| 6,916,296 B2 | 7/2005 | Soring et al. | |
| 6,960,173 B2 | 11/2005 | Babaev | |
| 6,964,647 B1* | 11/2005 | Babaev | 604/22 |
| 7,316,664 B2 | 1/2008 | Kadziauskas et al. | |
| 2002/0080206 A1* | 6/2002 | Lin | 347/29 |
| 2002/0177846 A1 | 11/2002 | Mulier et al. | |
| 2003/0195644 A1* | 10/2003 | Borders et al. | 700/90 |
| 2003/0236560 A1 | 12/2003 | Babaev | |
| 2004/0028552 A1 | 2/2004 | Bhardwaj et al. | |
| 2004/0030254 A1 | 2/2004 | Babaev | |
| 2004/0034982 A1* | 2/2004 | Wieber et al. | 29/428 |
| 2004/0055376 A1* | 3/2004 | Thompson et al. | 73/204.22 |
| 2004/0186384 A1 | 9/2004 | Babaev | |
| 2006/0025716 A1 | 2/2006 | Babaev | |
| 2006/0058710 A1 | 3/2006 | Babaev | |

FOREIGN PATENT DOCUMENTS

| | | |
|---|---|---|
| EP | 0 437 155 B1 | 2/1990 |
| EP | 416106 | 3/1991 |
| EP | 0 657 226 B1 | 11/1994 |
| GB | 2 099 710 A | 12/1982 |
| GB | 2 101 500 A | 1/1983 |
| JP | 2000237275 A2 | 9/2000 |
| SU | 1106485 | 10/1982 |
| SU | 11064585 A | 10/1982 |
| SU | 1827239 | 5/1990 |
| WO | WO 96/35383 | 11/1996 |
| WO | 97/17933 | 5/1997 |
| WO | WO-02/24150 | 3/2002 |
| WO | WO-02/28350 | 4/2002 |

OTHER PUBLICATIONS

Design and Application of Low-Frequency Ultrasound and Its Combination With Laser Radiation in Surgery and Therapy—Critical Reviews in Biomedical Engineering; 2001; pp. 502-519.

European Search Report corresponding to EPO Appln. No. 01973544.8-2107-US0130096.

XP002294548, Abstract corresponding to SU 914099.

Ennis et al., Ostomy/Wound Management 51(8):24-39 (2005).

U.S. Appl. No. 90/007,613, filed Jul. 5, 2005, Babaev.

Image File Wrapper for U.S. Appl. No. 11/168,620, filed Jun. 27, 2005.

* cited by examiner

REMOVABLE APPLICATOR NOZZLE FOR ULTRASOUND WOUND THERAPY DEVICE

RELATED APPLICATIONS

This application is a continuation-in-part of and claims priority to U.S. patent application Ser. No. 11/168620, filed Jun. 27, 2005, which claims priority to U.S. Provisional Patent Application Ser. No. 60/693560, filed on Jun. 23, 2005. The contents of each of the foregoing applications are hereby incorporated by reference in their entirety.

BACKGROUND

Ultrasound waves have been widely used in medical applications. For example, ultrasound waves have been used for diagnostic and therapeutic purposes, as well as in many industrial applications. One diagnostic use of ultrasound waves includes using ultrasonic waves to detect underlying structures in an object or a human tissue. In this procedure, an ultrasonic transducer is placed in contact with the object or tissue and a coupling medium is used to help efficiently transmit the high frequency (1-10 MHz) ultrasonic waves that are directed into the tissue. Upon contact with various underlying structures, the waves are reflected back to a receiver adjacent the transducer. By comparison of the signals of the ultrasonic wave as sent with the reflected ultrasonic wave as received, an image of the underlying structure can be produced. This technique is particularly useful for identifying boundaries between components of tissue and can be used to detect irregular masses, tumors, and the like.

In addition to diagnostic uses, ultrasonic energy can be used for therapeutic purposes. Two therapeutic medical uses of ultrasound waves include aerosol mist production and contact physiotherapy. Aerosol mist production makes use of a nebulizer or inhaler to produce an aerosol mist for creating a humid environment and delivering drugs to the lungs. Ultrasonic nebulizers operate by the passage of ultrasound waves of sufficient intensity through a liquid, the waves being directed at an air-liquid interface of the liquid at a point underneath or within the liquid. Liquid particles are ejected from the surface of the liquid into the surrounding air following the disintegration of capillary waves produced by the ultrasound. This technique can produce a very fine dense fog or mist. Aerosol mists produced by ultrasound are preferred over aerosol mists produced by other methods because a smaller particle size of aerosol can be obtained with the ultrasonic waves. Although ultrasonic nebulizers represent an improvement over other nebulizer technologies, the use of ultrasound energy in this context has certain limitations. One of the major shortcomings of inhalers and nebulizers is that the aerosol mist produced cannot be directed to a target area without an air stream. However, the use of an air stream decreases the efficiency of ultrasound, thus limiting the utility and therapeutic applicability of ultrasound nebulizers.

Ultrasonic sprayers such as those sold by Sonic and Materials Inc., Misonix Inc., Sono-Tek Inc. (see, for example, U.S. Pat. Nos. 4,153,201, 4,655,393, and 5,516,043) operate by passing liquid through a central orifice of an ultrasound instrument-tip. Major disadvantages of these sprayers include non-uniform particle size, heating of liquid flow, and less efficiency of the ultrasound waves.

Contact physiotherapy applies ultrasonic waves directly to tissue in an attempt to produce a physical change in the tissue. In conventional ultrasound physiotherapy, an ultrasonic wave contacts the tissue via a coupling medium. Ultrasonic waves produced by the transducer travel through the coupling medium and into the tissue. The coupling medium is typically a bath of liquid, a jelly applied to the surface to be treated, or a water-filled balloon. Conventional techniques provide ultrasonic waves having an intensity of about 0.25 w/cm$^2$ to about 3 w/cm$^2$ at a frequency of about 0.8 to about 3 Megahertz. The treatment is applied to a skin surface for about 1 to about 30 minutes, for multiple times a week. The coupling medium can provide a cooling effect which dissipates some of the energy produced by the ultrasonic transducer.

More importantly, a coupling medium or direct contact between the tissue and ultrasonic transducer is desirable to transmit the ultrasonic waves from the transducer to the skin surface because ambient air is a relatively poor medium for the propagation of ultrasonic waves.

Several beneficial effects have been reported from contact ultrasound physiotherapy, such as, for example, the following: local improvement of the blood circulation, heating of the tissue, accelerated enzyme activity, muscle relaxation, pain reduction, and enhancement of natural healing processes. Despite these beneficial effects, current techniques of medical physiotherapy using ultrasonic waves are limited because the efficient transmission of the ultrasonic waves used in these technologies requires direct contact between the device and the tissue to be treated. This direct contact, even if via a coupling medium, may be undesirable for certain medical applications.

The requirement of direct contact, with or without a coupling medium, makes current contact physiotherapy methods and devices undesirable and suboptimal for many therapeutic uses. Although some tissue conditions may be physically accessible to contact ultrasound devices, the use of contact-mediated devices would be impractical and undesirable. For example, fresh or open wounds resulting from, for example, trauma, burns, and surgical interventions are not suitable for direct contact ultrasound treatment because of the structural nature of the open wound and the painful condition associated with those wounds. Moreover, conventional contact ultrasound may have a destructive effect on these types of open wounds due to the close proximity of an oscillating tip of an ultrasonic transducer relative to the already damaged tissue surface. Furthermore, open wounds are susceptible to infection and may already harbor significant bacterial and other microbial growth. Direct contact with the wound may increase the risk of contamination of the wound and/or the risk of contaminating the device or its operator.

Commonly-owned U.S. Pat. No. 6,569,099 discloses an ultrasonic device and method for wound treatment, the entire contents of which are incorporated herein by reference. This patent discloses, inter alia, a device that sprays liquid particles to a wound via an applicator. The liquid particles provide a medium for propagation of the ultrasonic waves. In contrast to prior art methods and devices for contact, ultrasonic physiotherapy, the applicators and devices disclosed in the present application, as well as the devices disclosed in U.S Pat. No. 6,569,099, provide non-contact methods for delivering ultrasonic energy via a liquid mist.

As can be appreciated, an improved applicator may be desired to produce a more reliable and consistent flow of liquid particles to a wound bed or site. The present invention provides an improved applicator that can be used in non-contact ultrasound therapy for the treatment of wounds.

SUMMARY

The present disclosure generally relates to the field of ultrasound wound therapy devices, and more particularly relates to a removable applicator nozzle for enabling a fluid to be sprayed towards a patient, thus providing a medium for ultrasonic waves to travel through and penetrate the tissue to a beneficial depth to provide bactericidal, therapeutic and other effects. The fluid may also have beneficial properties including bactericidal and/or therapeutic effects. Without being bound by theory, the beneficial properties of the ultrasonic energy and/or fluid may be due to action of the fluid on the surface of the wound and/or effects of the fluid following penetration of the tissue to a beneficial depth.

According to an aspect of the present disclosure, a removable applicator nozzle for use in treating a wound is provided. The removable applicator nozzle (referred to interchangeably as an applicator) includes a nozzle, a valve and a cup portion. The nozzle includes a proximal portion, a distal opening and a valve interface. The proximal portion of the nozzle is engagable with a portion of an ultrasound wound therapy device. The distal opening of the nozzle allows at least a portion of a transducer tip of the ultrasound wound therapy device to pass therethrough. The valve is engagable with the valve interface of the nozzle and the valve selectively allows fluid to flow therethrough. The cup portion includes an aperture and may optionally include a puncturing device. The aperture is engagable with the valve and the puncturing device is able to puncture a bottle or other fluid container that is inserted on the cup portion.

In use, a bottle containing fluid is placed on the cup portion, and the puncturing device punctures a hole in the bottle, which allows fluid contained in the bottle to exit the bottle. The fluid flows out of the bottle, through the valve and onto a portion of the tip of the ultrasound wound therapy device. The fluid drips from the nozzle to a top surface of the transducer tip, drips/wraps around the transducer tip and then a vacuum effect takes place which moves the fluid forward to a distal end face of the transducer tip.

It is envisioned for the fluid to drip onto a portion of the ultrasound wound therapy device that is proximal to the distal-most portion of the tip of the ultrasound wound therapy device. It is also envisioned for the fluid to drip on or about the most distal-most portion of the tip of the ultrasound wound therapy device.

In another aspect, the invention provides methods for treating a wound. The methods are used to deliver ultrasonic energy at a non-contact distance through a fluid spray to a wound. The method comprises providing an ultrasound wound therapy device including a transducer which emits ultrasonic energy and providing an applicator. The applicator comprises a nozzle including a proximal portion, a distal opening and a valve interface. The proximal portion of the nozzle is engagable with a portion of an ultrasound wound therapy device, and the distal opening allows at least a portion of a transducer tip of the ultrasound wound therapy device to pass therethrough. The applicator further comprises a valve comprising a valve opening, an upper portion and a lower portion. The lower portion is engagable with the valve interface of the nozzle, and the upper portion is in fluid communication with a fluid source. The valve opening selectively allows fluid to flow therethrough. Once the valve has been opened and fluid has been permitted to flow to the transducer tip, the method includes activating the transducer to emit ultrasonic energy. Fluid that flows onto a surface of the activated transducer creates a spray, and ultrasonic energy and the fluid spray are emitted through the applicator and out of the device. The emitted energy and spray are delivered to a wound.

In certain embodiments, the transducer tip vibrates at a rate of about 1 kHz to about 10,000 MHz. In certain embodiments, the transducer tip vibrates at a rate of about 30 kHz to about 50 kHz. In certain other embodiments, the transducer tip vibrates at a rate of about 40 kHz to about 45 kHz.

In another aspect, the invention provides a kit. The kit comprises an applicator, and a bottle containing a fluid. The applicator is an applicator according to the present invention. For example, the applicator includes a nozzle engagable with a portion of an ultrasound wound therapy device, a valve, and a cup portion.

The bottle is designed for use with an ultrasound wound therapy device. The bottle is designed for use, for example, with an applicator according to the present invention or for use with related applicators. When designed for use with an applicator according to the present invention, the bottle is sized and shaped to fit into a cup portion of the applicator. The bottle is made of a material, for example plastic, so that it can be punctured with a puncturing device or with a needle. The bottle includes a fluid for use with an ultrasound wound therapy device. The fluid is sterilized so that, in use, a spray of a sterile solution can be administered to patients. Exemplary fluids include, but are not limited to, sterile water, saline solution, oil, oxygenated water, or other isotonic or hypertonic solutions. Exemplary fluids may, in certain embodiments, further include drugs (e.g., therapeutic agents) such as antibiotics, anti-fungals, anti-virals, growth factors, analgesics, narcotics, and the like, formulated in any of the foregoing fluids or in other pharmaceutically acceptable fluids appropriate for the formulation of the particular drug. However, in certain embodiments, the fluid does not include a drug.

In certain embodiments, the kit includes directions for use. In certain embodiments, the kit includes one or more sanitary swabs for cleaning one or more of the following: the surface of the bottle, the cup portion of the applicator, the puncturing device, the transducer assembly, or another portion of the ultrasound wound therapy device.

DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION OF VARIOUS EMBODIMENTS

Figure 1:
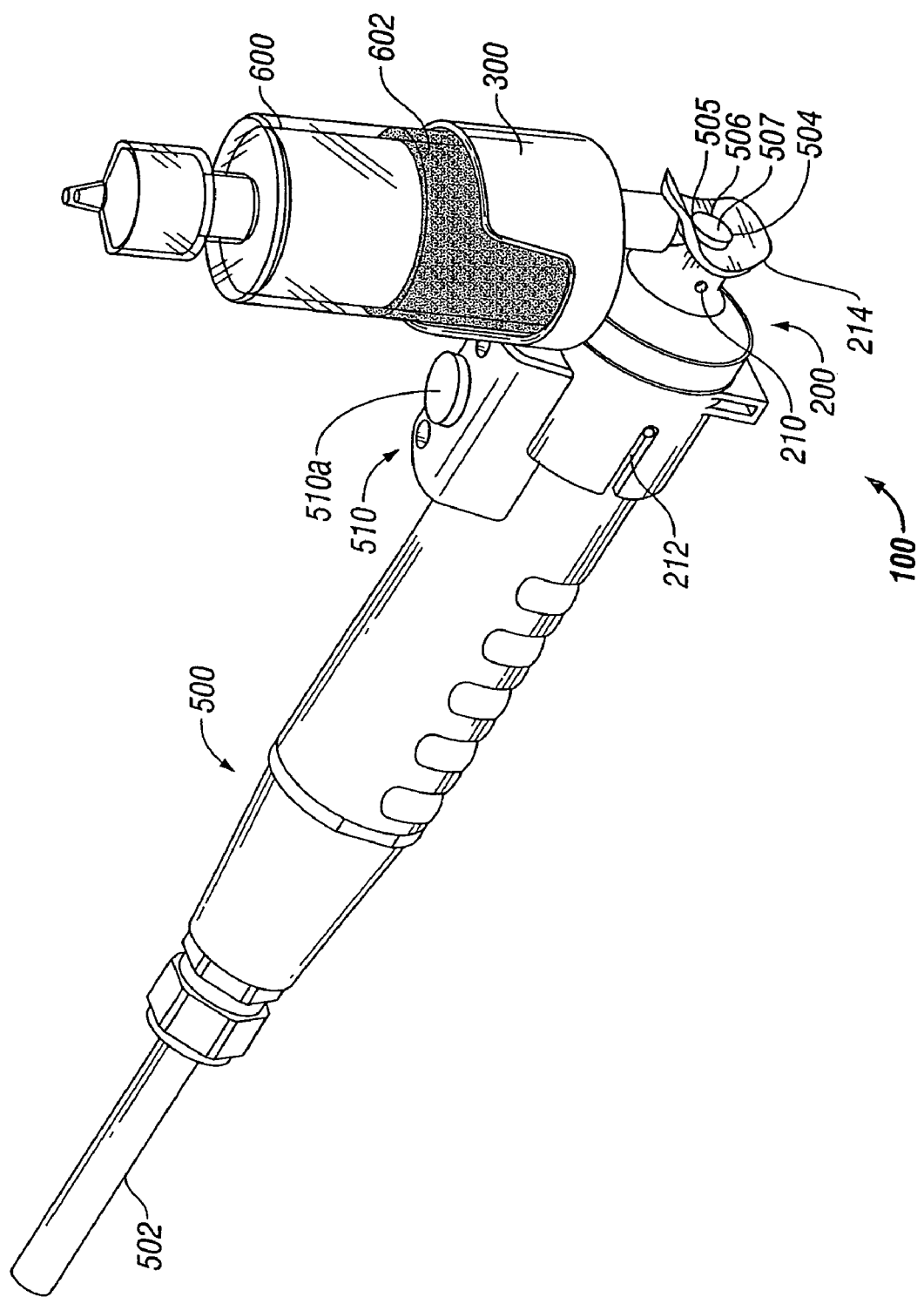
FIG. 1 is a perspective view of the removable applicator nozzle of the present disclosure including a nozzle, a cup, and a valve, the removable applicator nozzle being illustrated operatively attached to a transducer of an ultrasound wound therapy device and with a bottle inserted therein.

Embodiments of the presently disclosed removable applicator nozzle will now be described in detail with reference to the drawing figures wherein like reference numerals identify similar or identical elements. As used herein and as is traditional, the term "distal" refers to that portion which is farthest from the user while the term "proximal" refers to that portion which is closest to the user. Further, as used herein, the word "wound" refers to surface wounds, such as burns and skin lesions; internal wounds, such as ulcers and surgical cuts due to surgery; surgical incisions; injuries, including broken bones; and other conditions or applications requiring treatment using ultrasound wound therapy.

Figure 2:
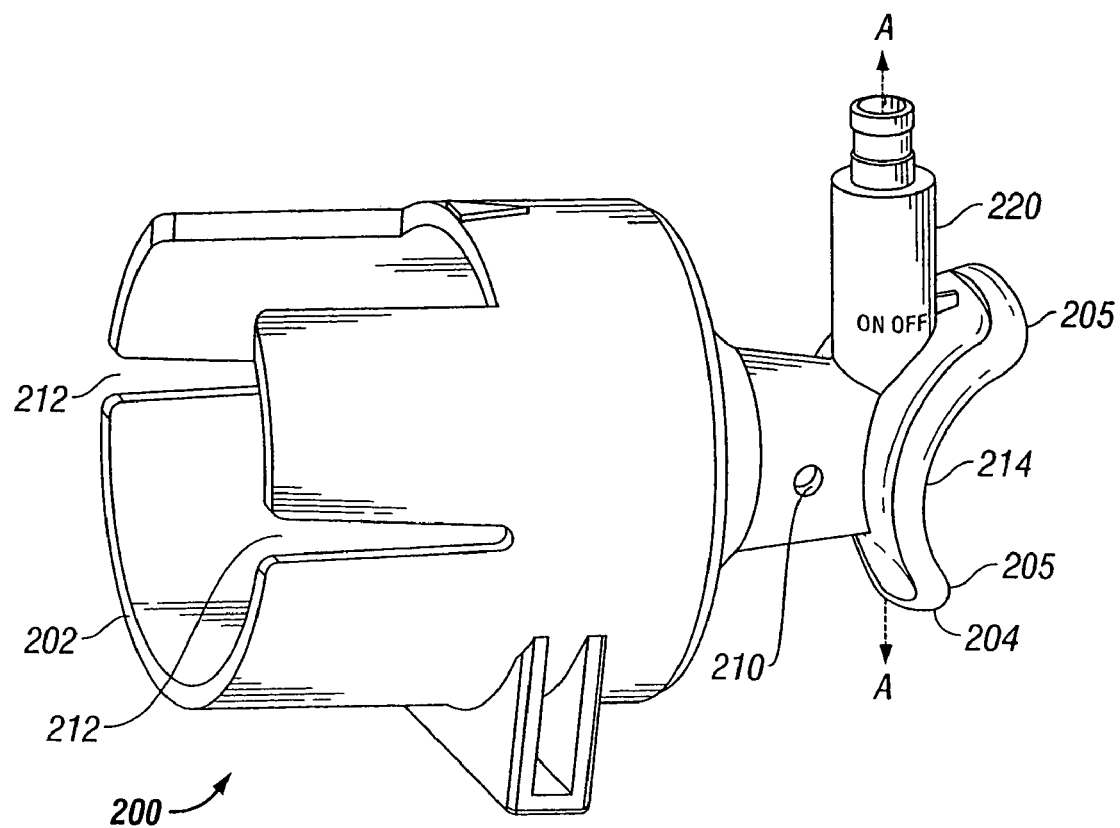
FIG. 2 is a perspective view of the removable applicator nozzle of FIG. 1.
Figure 3:
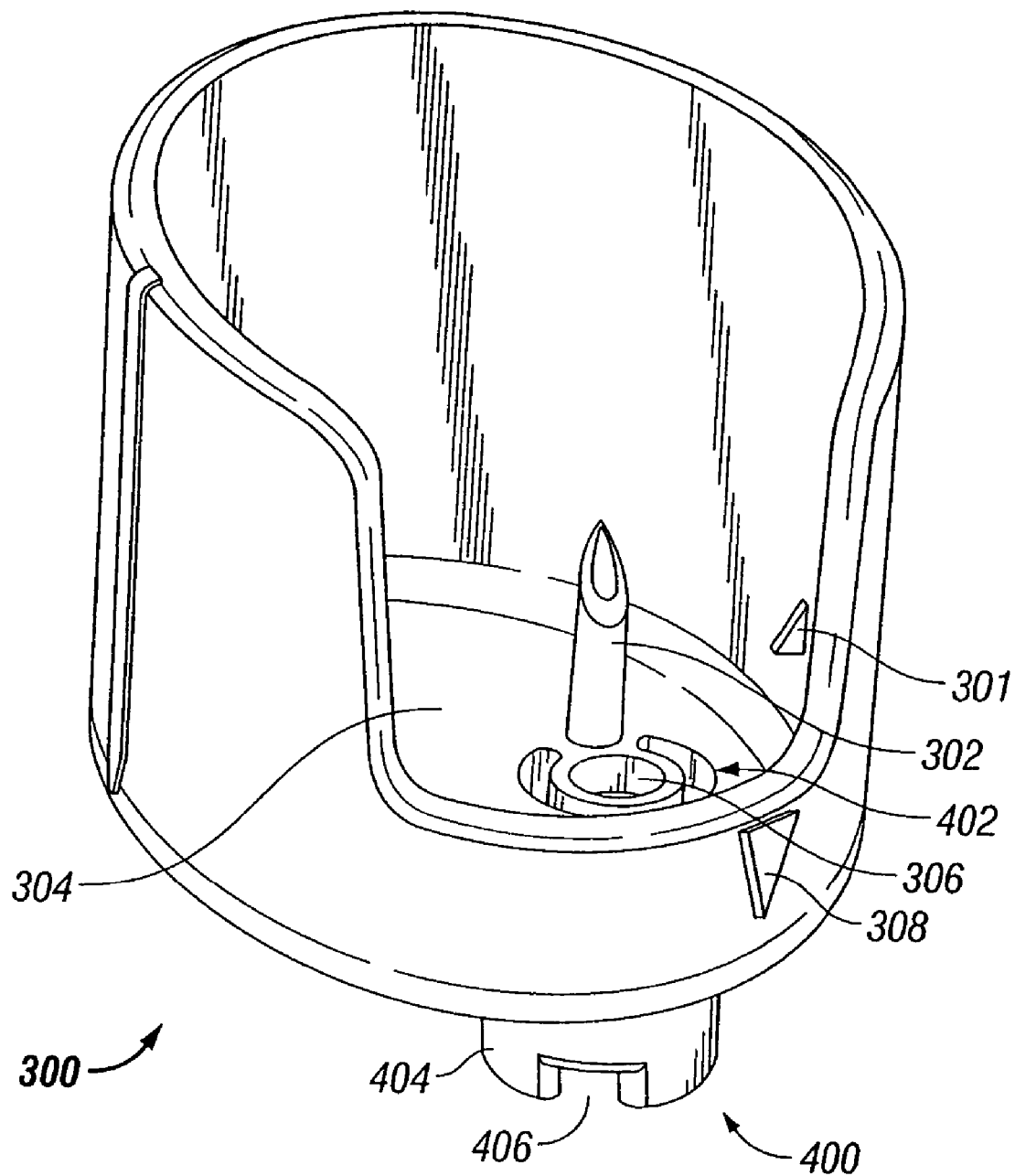
FIG. 3 is a perspective view of the cup and the valve of FIG. 1.

In the figures, a removable applicator nozzle or applicator according to an aspect of the present disclosure is generally designated as reference numeral 100. Applicator 100 generally includes a nozzle 200 (FIG. 2), a cup 300 (FIG. 3), and a valve 400 (FIG. 3). Referring to FIG. 2, the nozzle 200 includes a proximal portion 202, a distal portion 204, a plurality of alignment slots 212, a distal opening 214, and a valve interface 220 (also shown in FIG. 6). In an alternate embodiment, the applicator 100 includes a chip housing 230 (see FIGS. 4 and 5). The portion of the nozzle 200 that extends the farthest distally is distal tip 205.

It is envisioned for the applicator 100 in accordance with the present disclosure to be designed for use with an ultrasound wound therapy device, such as the device described in U.S. Pat. No. 6,569,099, the entire contents of which are incorporated herein by reference. The present disclosure is also related to U.S. Pat. Nos. 6,478,754 and 6,663,554 and U.S. patent application Ser. No. 09/684,044, the entire contents of both patents and the patent application are incorporated herein by reference.

An exemplary ultrasound wound therapy device includes a transducer assembly 500 operatively connected to a generator (not shown). As described herein, the ultrasound wound therapy device may further include an applicator 100 that can be interconnected to the transducer assembly. Briefly, the generator includes the components necessary to supply power to the transducer assembly, and also contains a graphical user interface (GUI) for displaying information helpful to the operator. The generator consists of three major functional sections: the AC MAINS, the main board, and the GUI board. The local AC MAINS is connected to an appliance inlet with a hospital grade detachable power cord. The appliance inlet is a power entry module listed for medical applications. In certain embodiments, the appliance inlet is a power entry module with an 115V/230V voltage selection, and is designed to operate on 115 Vac and 60 Hz (e.g., for operation in North America) or 230 Vac and 50 Hz (e.g., for operation in Europe).

The MAIN board converts the secondary output voltage from the MAINS transformer to the low voltage power rails for the internal electronics and the drive voltage for the drive electronics to the transducer assembly. The MAIN board contains a microprocessor that controls, measures, and monitors the drive electronics. The transducer assembly connects to the MAIN board. The microprocessor, referred to as the engine, monitors the performance of the system and communicates the information to a second microprocessor located on the GUI board. In certain embodiments, the engine communicates to the second microprocessor via a RS-232 communication link. In certain embodiments, the electronics drive the ultrasound portion of the drive electronics with a push-pull converter that has a feedback loop with a Phase Locked Loop (PLL) to track the center frequency of the ultrasound components.

The GUI board provides the graphical user interface for the operator. A custom membrane switch panel with, for example 6 keys, allows the operator to select the functions and operating parameters of the system. A purchased graphical LCD display, connected to the GUI board, can be used to display information to the operator. For example, information about the system's status, mode of operation, and treatment time can be displayed via the LCD. The GUI may have a back light generator for the LCD on it. The GUI microprocessor runs the system by controlling the human interface and running the various algorithms to control the operation of the system. For example, a treatment algorithm can be run on the GUI microprocessor. In certain embodiments, the ultrasound wound therapy device may include one or more of a timer to record total treatment time, a timer to count-down from a selected treatment time to zero, and an alarm to indicate that the total treatment time has elapsed or that there is a problem with some component of the device.

Now referring to FIG. 3, the cup 300 includes a puncturing device 302, a lower portion 304 with an aperture 306 extending therethrough, and may include an alignment structure 308. The cup 300 may be designed to hold at least a portion of a bottle 600 (FIG. 1) therein. The bottle 600 generally holds a fluid 602, which may be saline. The fluid may alternatively be sterile water or some other isotonic or hypertonic solution or combination of solutions. The fluid may consist entirely or essentially of the saline or other similar solution, or the fluid may optionally include a therapeutic drug. The fluid may optionally be sterilized. The cup 300 may also include structure, such as indent(s) 301, on the lower inside surface of the bottle 600 as shown by FIG. 3 for enhancing the grip and fit of the bottle 600 within the cup 300. When included, indent(s) 301 are configured for damaging the bottle 600 upon removal of the bottle 600 from the cup 300, thereby preventing reuse of the bottle 600.

The valve 400 is also illustrated in FIG. 3. The valve 400 includes an upper portion 402, a lower portion 404 and a slot 406. The valve 400 selectively allows the fluid 602 from the bottle 600 to pass therethrough and towards the nozzle 200. In certain embodiments, it is envisioned for the valve 400 to be separate or removable from the applicator 100. For example, a removable valve may be designed to disengage from the applicator when the applicator is detached from the remainder of the ultrasound wound therapy device following use. Such a design and valve configuration could be used to prevent reuse of an applicator. In other embodiments, the valve 400 is not separate or removable, but rather is included and integrated with the cup 300.

Referring to FIGS. 1-3, the nozzle 200, the cup 300 and the valve 400 mechanically engage with one another to form the applicator 100. Specifically, the lower portion 404 of the valve 400 fits over the valve interface 220 of nozzle 200; the upper portion 402 of the valve 400 fits into the aperture 306 of the cup 300. When mechanically engaged, the cup 300 is capable of turning approximately 90° with respect to an axis A-A, as defined by the valve interface 220 (FIG. 2). Turning the cup 300 adjusts the valve 400 from a closed position where the fluid 602 cannot flow through, to an open position which provides a passage for the flow of the fluid 602. Turning the cup 300 back towards its original position closes the valve 400.

With specific reference to FIGS. 1, 4 and 5, the applicator 100 is mechanically connectable with a transducer assembly 500 of an ultrasound wound therapy device, hereinafter referred to as a transducer assembly. When activated, the transducer assembly 500 produces ultrasonic waves having a frequency of about 1 kHz to about 10,000 MHz. The ultrasonic waves deliver ultrasonic energy to a wound surface, including below the wound surface, via a spray which acts as the coupling agent for the ultrasonic energy as further described below. The ultrasonic energy provides bactericidal, therapeutic and other effects for decreasing the healing time for the wound as disclosed by U.S. Pat. No. 6,569,099, the entire contents of which are incorporated herein by reference. Without being bound by theory, the liquid spray delivered to the wound may also have bactericidal, therapeutic, and other effects on wound healing at the surface of and/or below the surface of the wound. In use, ultrasound energy emitted from the transducer and a fluid spray produced when fluid is dripped on a face of the transducer are delivered to a wound.

Specifically, the proximal portion 202 of the nozzle 200 slides over a distal portion 504 of the transducer assembly 500. The plurality of aligning slots 212 (illustrated as two slots) of the nozzle 200 engage with a plurality of aligning pins 508 (FIG. 4) of the transducer assembly 500. When connected, the distal end 506 of a tip 505 of the transducer assembly 500 may extend distally of the distal opening 214 of the nozzle 200 but not to a location that is distal of the tip 205 of the nozzle 200. That is, when the transducer assembly 500 is inserted through the applicator 100, the distal end 504 of the transducer assembly 500 extends between the distal opening 214 and the distal tip 205 of the nozzle 200, such that the distal dip 205 of the nozzle 200 is coaxially disposed about the distal end 504 of the transducer assembly 500.

In use, the cup 300 is inserted onto the "valve" 400 (as shown in FIG. 3) and the valve 400 is inserted onto the valve interface 220 of the nozzle 200. The transducer assembly 500 is then aligned and coupled with the nozzle 200, via aligning slots 212 and alignment pins 508. The distal end 506 of the transducer assembly 500 is inserted through the proximal portion 202 of the nozzle 200, continues through the distal portion 204 of the nozzle 200, and out through the distal opening 214 of the nozzle 200. The bottle 600 may then be placed into the cup 300. Upon insertion of the bottle 600 into the cup 300, the puncturing device 302 of the cup 300 punctures a hole in the bottle 600. The aligning structure 308 may assist the user in properly positioning the bottle 600 in the cup 300. In certain embodiments, it is envisioned for the bottle 600 to be inserted into the cup 300 prior to the applicator 100 being coupled with the transducer assembly 500. The insertion of the cup 300 and valve 400 into the nozzle 200, the coupling of the applicator 100 and the transducer assembly 500, and the insertion of the bottle 600 into the cup 300 allow the applicator 100 to be utilized vis-a-vis the transducer assembly 500.

To utilize the applicator 100 with the transducer assembly 500, a user turns the cup 300 approximately 90°. The turning of the cup 300 "opens" the "valve" 400 by aligning a valve opening 222 (FIG. 6) with the hole in the nozzle 200 and allows the fluid 602 to pass through the valve 400. The nozzle 200 is specifically designed such that the fluid 602 drips through the valve interface 220 of the nozzle 200 and onto the tip 505 of the transducer assembly 500. The fluid 602 drips onto a portion of the tip 505 that is proximal the location of the distal end 506 of the tip 505 of the transducer assembly 500.

In a particularly useful embodiment, the valve opening 222 (FIG. 6) is appropriately sized to allow a desired amount of fluid 602 to pass therethrough such that the fluid 602 that drips onto the tip 505 of the transducer assembly 500 can wrap around the circumference of the tip 505. Such an effect is known as the Babaev effect, or vacuum effect, and creates a capillary action that wicks or applies the fluid 602 around the circumference of the tip 505 of the transducer assembly 500.

It is envisioned for the diameter of the valve opening 222 to be in the range of about 0.027 inches to about 0.037 inches and may be in the more specific range of about 0.031 inches to about 0.033 inches. Additionally, this size valve opening 222 may generate relatively uniform particle sizes of fluid 602. The particle sizes may be approximately equal to 60 µm in diameter. For example, the approximately uniform sized particles may be approximately equal to 40 µm, 45 µm, 50 µm, 55 µm, 60 µm, or 65 µm in diameter. It is also envisioned for the fluid 602 to drip onto a front face 507 of the tip 505 of the transducer assembly 500, as shown by FIG. 4a of U.S. Pat. No. 6,569,099. In use, it is envisioned for the fluid to drip onto a front face of the vibrating transducer tip.

Once the valve is opened and fluid begins to drip onto the transducer, a delay is needed for the fluid to coat the tip of the transducer. Thus, in certain embodiments, a user may wait, for example for approximately three seconds, for the fluid 602 to coat the circumference of the tip 505 of the transducer assembly 500 before he activates the transducer assembly 500. Thus, in certain embodiments, the user opens the valve and allows fluid to begin to coat the transducer assembly prior to activating the transducer (e.g., prior to turning the transducer on). To activate the transducer assembly 500, the user engages the switch 510. Two switches 510a, 510b are depicted in the figures (FIG. 1; and FIGS. 4 and 5, respectively) and other types of switches 510 are also envisioned and are within the scope of the present disclosure. Upon activation of the switch 510, the tip 505 of the transducer assembly 500 is displaced between about 60 µm to about 70 µm as the tip 505 vibrates at a rate of about 1 kHz to about 10,000 MHz. In certain embodiments, the transducer tip vibrates at a rate of about 30 kHz to about 50 kHz, or at a rate of about 40 kHz to about 45 kHz. In certain embodiments, the transducer tip vibrates at a rate of about 40 kHz. In any of the foregoing, an exemplary ultrasound wound treatment device modulates the transducer assembly so that the transducer tip vibrates at a given rate that varies by less than or equal to plus or minus 1 kHz.

Such a displacement provides the energy levels needed to provide therapeutic benefits and may minimize the aerosolization of bacteria and/or other tissue exudates. The displacement of the tip 505 causes a vacuum effect between the tip 505 of the transducer assembly 500 and the distal opening 214 of the nozzle 200, which moves the fluid 602 from the circumference of the tip 505 distally out through the distal opening 214 of the nozzle 200. Upon exiting the applicator 100, the fluid 602 is in the form of a mist. Such a fluid mist medium ameliorates the dissipation effect that ultrasonic energy typically undergoes as ultrasonic waves travel in air. Specifically, the impedance of air makes it a relatively poor medium for the transfer of ultrasound energy. The use of a liquid mist provides improved energy transfer properties, and thus promotes more efficient ultrasound energy transfer. At the same time, the use of a liquid mist, as described for the non-contact devices disclosed herein, avoids the need for direct contact with patient tissue.

The separation distance between the free end surface of the transducer tip 505 and the surface or object to be sprayed should be a non-contact distance of at least 0.1 inches (2.5 mm). Preferably, the separation distance is from about 2.5 mm to about 51 cm, more preferably, from about 15 mm to about 25 mm. In certain embodiments, the applicator nozzle extends distally beyond the transducer tip. Such a design has numerous benefits including the prevention of inadvertent patient or operator contact with the transducer tip. The non-contact distance can similarly be described as the distance between the distal-most edge 205 of the nozzle 200 and the surface or object to be sprayed. In certain embodiments, the non-contact distance from the distal-most edge 205 of the applicator nozzle 200 is at least about 5 mm. In other embodiments, the non-contact distance from the distal-most edge 205 of the applicator nozzle 200 is from about 5 mm to about 15 mm.

The fluid 602 to be sprayed and provided within the bottle 600 can be any appropriate carrier, such as saline, water (regular or distilled), or oil to be applied to tissue, such as a vegetable, peanut, or canola oil, optionally with a soluble pharmaceutical (e.g., an antibiotic), antiseptic, conditioner, surfactant, emollient, or other active ingredient. The fluid 602 can also be a combination of two or more fluids and/or substances having microscopic particles, such as powder and the like. Exemplary fluids include, but are not limited to, sterile water, saline solution, oil, oxygenated water, or other isotonic or hypertonic solutions. Exemplary fluids may, in certain embodiments, further include drugs (e.g., therapeutic agents) such as antibiotics, anti-fungals, anti-virals, growth factors, analgesics, narcotics, and the like, formulated in any of the foregoing fluids or in other pharmaceutically acceptable fluids appropriate for the formulation of the particular drug. However, in certain embodiments, the fluid does not include a drug. The fluid may be sterilized so that, in use, a spray of a sterile solution can be administered to patients.

As can be appreciated, the apparatus as described enables a gravity feed system for delivery of the fluid 602 to the transducer assembly 500. Such a system may not pressurize the fluid 602. Pressurization of the fluid 602 may create inconsistent particle size and/or velocity, which may create aerosolization.

It is envisioned for the bottle 600 of the present disclosure to be eliminated and/or replaced with another structure for delivering the fluid 602 to the transducer assembly 500, such as a fluid bag (not shown). In such an embodiment, the fluid 602 may optionally be delivered to the transducer assembly 500 in a pressurized state. Desirably, the pressurized fluid 602 in such an embodiment may be approximately equal to the pressure of the fluid 602 exiting the bottle 600, as in the previous embodiment.

This pressure may be relatively small and may be dictated by the pressure associated with gravity and the size opening of the valve opening 222. This type of arrangement, using a fluid bag as opposed to a bottle 600, may be useful in situations where the bottle 600 may interfere with accessing a particular site. It may also be useful to use a fluid bag in situations where the transducer assembly 500 is held in a general vertical orientation and/or to allow for a greater amount of fluid to be used (i.e., a fluid bag may be able to hold more fluid 602 than the bottle 600). Moreover, when the bottle 600 is replaced with a fluid bag (or another suitable replacement), the cup 300 and/or puncturing device 302 may not be necessary.

It is envisioned for a plurality of valve openings 222 to be included in the applicator 100. A plurality of valve openings 222 may be particularly useful to allow the tip 505 of the transducer assembly 500 to be evenly coated with fluid 602, especially when the transducer assembly 500 is orientated in a generally vertical direction.

It is envisioned for the applicator 100 to include an aligning structure (not shown) for creating a uniform gap between the tip 505 of the transducer assembly 500 and the distal opening 214 of the nozzle 200. This uniform gap may be in the range of about 10 mm to about 20 mm with 18 mm currently being used and may further ensure a proper vacuum effect between the tip 505 of the transducer assembly 500 and the distal opening 214 of the nozzle 200.

In certain embodiments, the applicator and/or ultrasound wound therapy device includes means for encouraging or requiring that the applicator 100 be replaced following a single use. Single use of the applicator 100 is recommended by the manufacturer to prevent non-sterile use and/or cross-contamination between patients. In one embodiment, a message can be displayed by an LCD or other display located on the ultrasound wound therapy device or on the applicator 100. The message would be displayed after a single use of the applicator 100, and the message would state that additional use of the applicator 100 is not allowed or recommended and that the applicator 100 should be replaced with another applicator 100. Alternatively, a light or alarm could be used to remind the operator to replace the applicator 100 after a single use.

The above messages and alarms are designed to remind and encourage compliance with the recommended use of the applicator 100 (e.g., the applicator should be used once and discarded). Alternatively or additionally, the applicator or ultrasound wound therapy device may include means for preventing applicator reuse. In other words, the applicator or ultrasound wound therapy device may include a mechanism that inhibits or prevents an operator from using a single applicator 100 to treat multiple patients and/or multiple wounds. One such exemplary means for preventing applicator reuse is depicted in FIGS. 4 and 5, and will be described in detail here. Other exemplary means are contemplated and are described throughout the present application.

Figure 4:
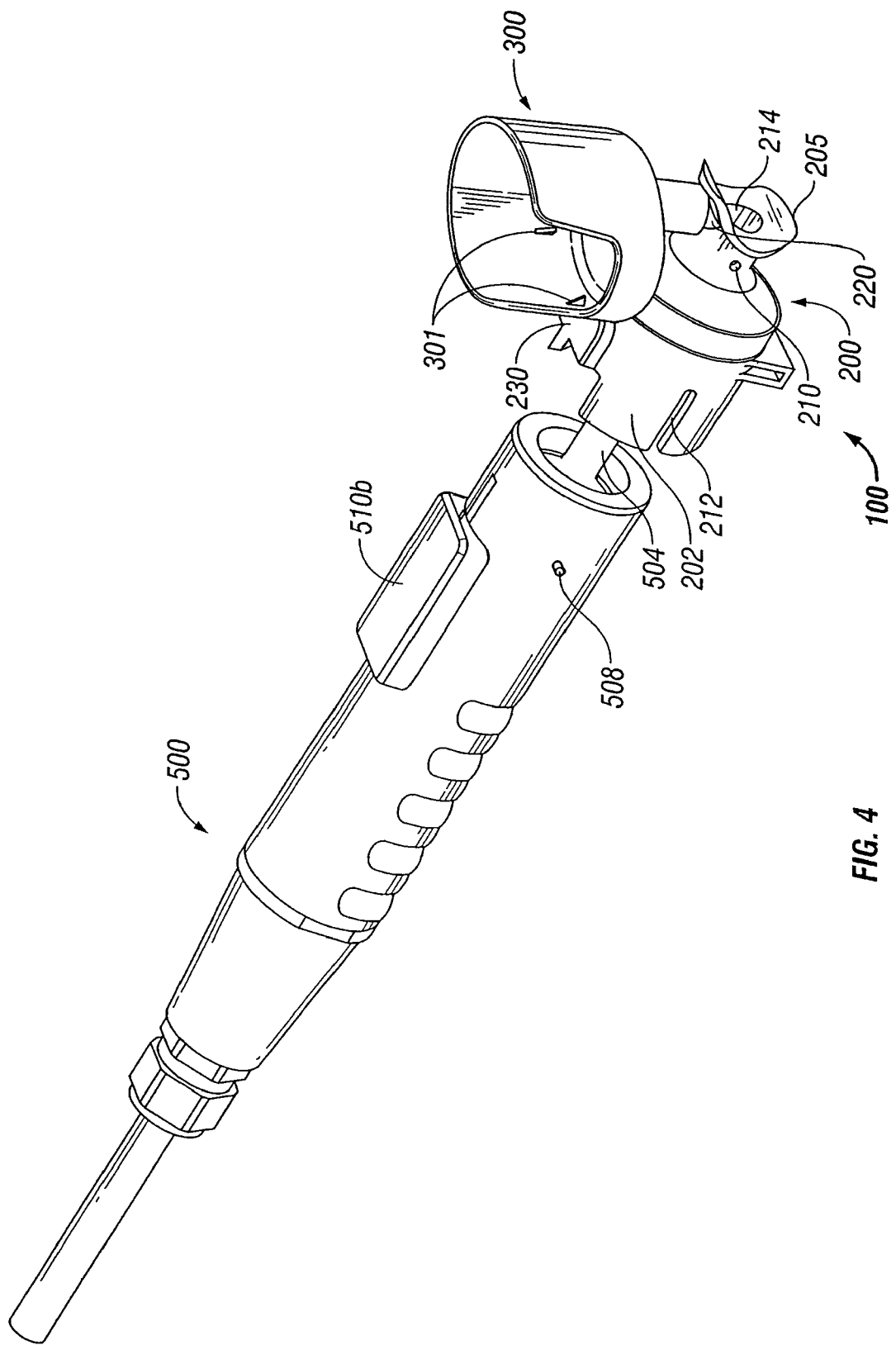
FIG. 4 is a perspective view of a removable applicator nozzle of an alternate embodiment partially inserted into a transducer of an ultrasound wound therapy device.
Figure 5:
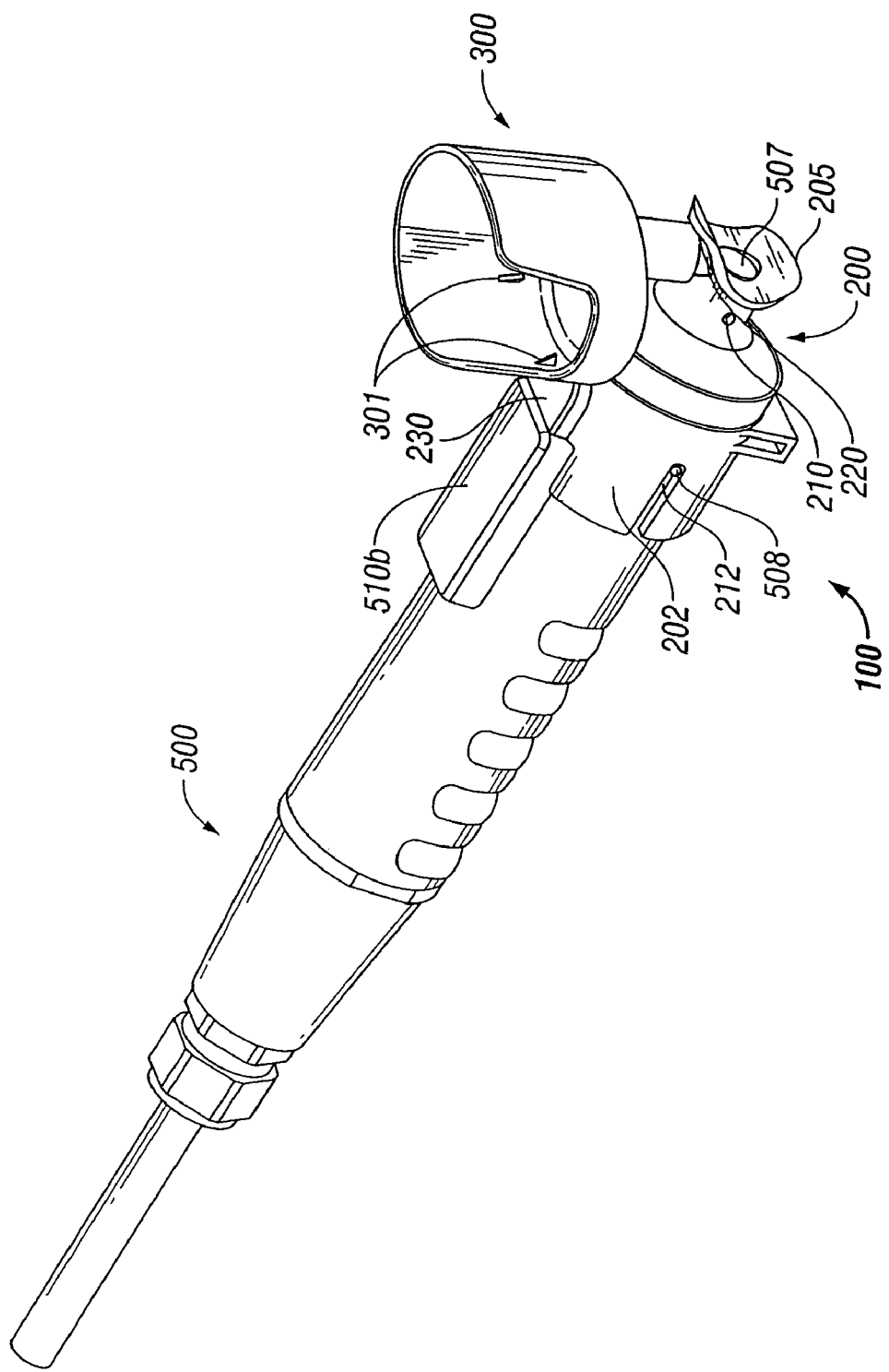
FIG. 5 is a perspective view of the removable applicator nozzle of FIG. 4 illustrated fully inserted into the transducer of FIG. 4.
Figure 6:
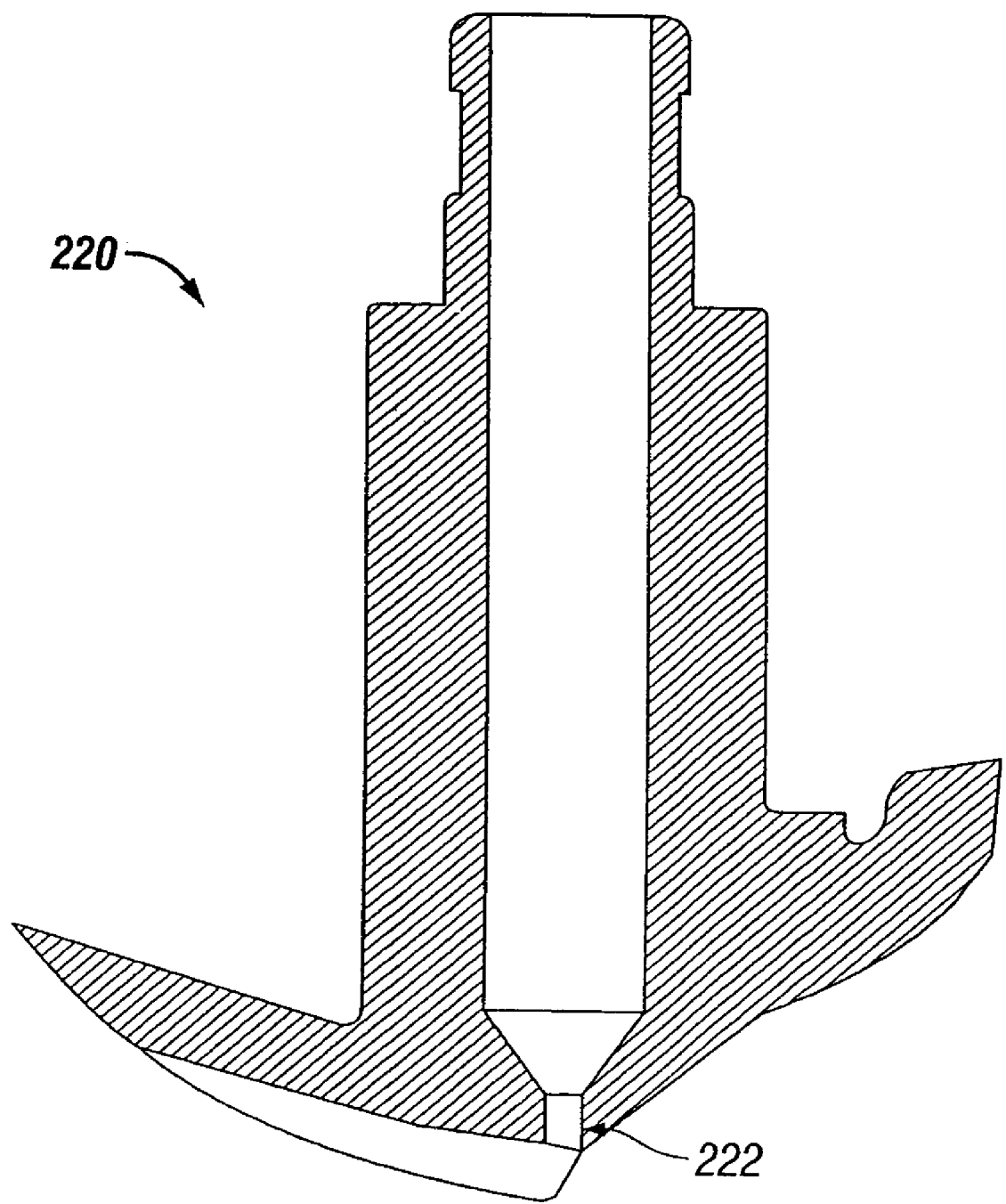
FIG. 6 is a cross-sectional view of a valve interface of the removable applicator nozzle of FIGS. 2 and 4.

An example of means to inhibit or prevent applicator reuse is depicted in FIGS. 4 and 5, an alternate embodiment of the applicator 100 which includes a chip housing 230. The chip housing 230 is keyed to interlock with the switch 510b of the transducer. A IC chip (not shown) is housed within the chip housing 230 and may be programmed to limit the number of times the applicator 100 is attached to the transducer assembly 500. Specifically, the IC chip can provide a mechanism to prevent reuse of the applicator 100 and/or to detect whether an applicator 100 has been previously used. In certain embodiments, this feature could help ensure that the applicator 100 is used only once or used for the treatment of only a single patient. Methods for preventing reuse of applicators for the treatment of multiple patients may help prevent potential non-sterile use and/or possible cross-contamination between patients.

In operation, the IC chip keeps count of the number of times the applicator 100 is attached to the transducer assembly 500. To prevent any reuse, once the applicator 100 has been attached, the IC chip transmits a signal to activate a solenoid or other device (e.g., software) for positioning a blocker to prevent the applicator 100, once removed, from being re-attached to the transducer assembly 500. The signal is transmitted after the applicator 100 is removed from the transducer assembly 500. Thus, an operator would be unable to use an applicator to treat a first patient, remove the applicator for cleaning, and subsequently reattach the used applicator to treat the same patient or a second patient. Other functions of the chip are also envisioned and are within the scope of the present disclosure. For example, in certain embodiments, the IC chip is programmed to limit applicator use to a certain number of times (e.g., to allow limited reuse).

The IC chip includes a power source, such as a battery, for powering the IC chip and/or the solenoid. The IC chip can be an ASIC and/or a combination of components, such as timing circuitry; memory for storing data and the number of times the applicator 100 has been attached to the transducer assembly 500; battery; solenoid; control circuitry for activating the solenoid; and a blocker in operative communication with the solenoid.

To count the number of times the applicator 100 is attached to the transducer assembly 500, the IC chip includes a toggle switch which is toggled every time the applicator 100 is attached to the transducer assembly 500. The toggling of the toggle switch is sensed by the IC chip and causes the IC chip to increase its count by one. If the count exceeds the predetermined number stored by the IC chip, following removal of the applicator 100, the IC chip transmits the signal for activating the solenoid or software as described above.

It is envisioned for the applicator 100 to include an LCD or other display for displaying the number of times the applicator 100 has been attached to the transducer assembly 500. A sterilization icon can also be displayed by the LCD or other display. The sterilization icon is selected from a group of pre-stored sterilization icons for informing the user that sterilization of the applicator 100 is or is not required, as well as for informing the user that sterilization of the applicator 100 is not recommended.

In certain embodiments of any of the foregoing aspects or embodiments of the invention, it is also envisioned for the switch 510 on the transducer assembly 500 to be able to simultaneously open/close the valve 400 and activate/deactivate the transducer assembly 500. When present, such a switch 510 would allow a user to effectively utilize the transducer assembly 500/applicator 100 in a singe motion (i.e., the user would not first have to turn the cup 300 and then activate the switch 510 of the transducer assembly 500). Use of a solenoid valve (not shown) is one mechanism envisioned to accomplish such utilization of the transducer assembly 500/applicator 100.

It is further envisioned, for any of the aspects and embodiments of the invention, for a single vent hole or a plurality of vent holes 210 (FIG. 2) to be disposed on the nozzle 200. For example, the nozzle may include two vent holes 210 configured on opposing sides of the nozzle 200 (e.g., one vent hole on each side of the nozzle). The vent holes 210 may help provide a pressure relationship for the fluid and may help provide the vacuum effect. In certain embodiments, the one or more vent holes have a diameter of about 0.05 inches to about 0.20 inches. In certain embodiments, the one or more vent holes have a diameter of about 0.075 inches, about 0.10 inches, or about 0.125 inches. In certain embodiments, the one or more vent holes have a diameter of about 0.10 inches. In certain embodiments of any of the foregoing, the diameter of the one or more vent holes varies by less than or equal to 0.01 inches from the recited diameter. It is also envisioned for the bottle 600 to include a plurality of vent holes (not shown).

As illustrated in FIGS. 1, 3, 4 and 5, the distal portion 204 of the nozzle 200 may be curved and/or contoured to focus ultrasonic energy as well as to complement standing wave potential. A similar characteristic is described in U.S. patent application Ser. No. 09/774,145, the entire contents of which are incorporated herein by reference. This shape may also limit inadvertent contact between the transducer tip 505 and a patient and/or a user of the transducer assembly 500.

The applicator 100 or ultrasound wound therapy device 500 can be provided with a laser or ultrasonic transducer for measuring the non-contact distance or stand-off distance from a wound surface. A feedback control mechanism can also be provided for indicating whether the measured non-contact distance is suitable for effecting optimum beneficial bactericidal, therapeutic and/or other effects. The feedback assembly is integrated with the transducer assembly and corresponding electronics housed within an ultrasonic generator for obtaining the measured non-contact distance data and processes the data to determine whether the measured non-contact distance is optimum for treatment purposes.

If the non-contact distance is determined not to be the optimum non-contact distance, the feedback control mechanism can sound an audible alarm or display a message on a display, such as the LCD display of the applicator 100. The alarm or message can indicate if the non-contact distance should be decreased or increased. If the applicator 100/ultrasound wound therapy device 500 is mounted to a robotic arm, the feedback control mechanism can in turn control the robotic arm for increasing or decreasing the non-contact distance.

For any of the foregoing or following applicators, methods, devices, and kits, the invention contemplates that any of a number of fluids may be used. Such fluids are delivered to a face of the transducer and ultrasound energy generated by the transducer produces a fluid spray. The fluid spray produced using the applicators and the methods of the present invention have a substantially uniform particle size. Exemplary fluids include, but are not limited to, sterile water, oxygenated water, saline solution, oil, or other isotonic or hypertonic solution. In certain embodiments, the fluid does not contain a therapeutic drug (e.g., the fluid is substantially free from a drug). In certain other embodiments, the fluid further includes one or more therapeutic drugs such as antibiotics, anti-fungals, anti-virals, growth factors, analgesics, narcotics, and the like. When the fluid includes a therapeutic drug, the drug may be formulated in any of the foregoing fluids (e.g., water, saline, etc), or the drug may be formulated in another pharmaceutically acceptable carrier appropriate for the formulation of the particular drug. In certain embodiments, the fluid (whether including a therapeutic drug or free from therapeutic drug) further includes one or more preservatives appropriate for extending the shelf-life of the fluid. In one embodiment of any of the foregoing, the fluid (whether including a therapeutic drug or free from therapeutic drug) is sterile (e.g., the fluid is sterilized prior to or after it is added to the bottle).

Regardless of the particular fluid selected for use, the fluid is applied to a surface of a transducer of an ultrasound wound therapy device, the ultrasound energy emitted from the transducer contacts the fluid and generates a fluid spray, and both the emitted ultrasound energy and the fluid spray are delivered to a wound. Following delivery to the wound, the ultrasound energy and/or the fluid spray penetrate the wound and have a therapeutic effect. Exemplary therapeutic effects include, but are not limited to, improve wound healing, decrease healing time, and reduce or prevent infection. The emitted ultrasound energy and the liquid spray are delivered to the wound at a non-contact distance from the wound. In other words, neither the transducer tip nor the nozzle contacts the wound.

In certain embodiments, the liquid spray is delivered at a temperature that does not result in substantial heating of the wound tissue. This is a significant advance over other methods and devices and provides significant improvements for patient comfort during treatment.

The present invention contemplates the use of numerous fluid containers to contain the fluid prior to application to the patient. In certain embodiments of any of the foregoing, the fluid is contained within a bottle. When a bottle is used to contain the fluid, the bottle may be sized and shaped to fit onto a cup of an applicator. An exemplary bottle 600 containing fluid 602 is shown in FIG. 1.

In certain other embodiments, other fluid containers are also contemplated. For example, a fluid bag may be used. A fluid bag, for example the types of bags often used to deliver intravenous fluids to patients, allows the delivery of a relatively large volume of liquid. A fluid bag may be especially useful for treating large wounds where longer treatment times and larger volumes of fluid are needed. When used, a fluid bag may be attached directly to the valve, for example, via a flexible tubing. In such embodiments, the cup portion of the applicator is optional and the fluid bag can be interconnected directly to the valve (e.g., such that the fluid bag is in fluid communication with the valve).

In certain other embodiments, a fluid container of virtually any size or shape is contemplated. However, given that larger containers are relatively heavy when filled with fluid, the fluid container may be placed on a counter-top, cart, or hung from a pole. In such embodiments, the fluid container may be attached directly to the valve, for example, via a flexible tubing. In such embodiments, the cup portion of the applicator is optional and the fluid container can be interconnected directly to the valve (e.g., such that the fluid bag is in fluid communication with the valve). In one embodiment, the fluid container rests or is affixed to the same cart upon which the ultrasound wound therapy device sits.

The applicators of the present invention provide substantial improvements for the treatment of wounds. The applicators provide for the production and delivery of a fluid spray of a more uniform particle size. Additionally, the applicators are disposable, and can be readily removed from the transducer body and changed between patients. In certain embodiments, the applicator is changed between each patient. Changing the applicator between uses, such that each patient's wounds are treated with a fresh applicator, prevents contamination between patients.

Given the potential benefits of using a new applicator between patients, certain embodiments of the present invention include means for preventing applicator reuse. An example of one such device, an IC chip, is detailed above. Thus, in one embodiment of any of the foregoing, the applicator and/or the ultrasound wound therapy device includes means for preventing re-use of the applicator. Further examples of devices and other means for preventing reuse of the applicator include a timer. A timer could be used to prevent the use of the device for greater than a specified, consecutive period of time. Once a particular pre-set time is exceeded, the device shuts off and cannot be restarted until the applicator is removed. Removal of the applicator and replacement with a new, as yet unused applicator, is necessary to re-set the timer and permit further use of the ultrasound wound therapy device. For example, the maximum total treatment time could be pre-set by the manufacturer for 35 minutes. Assuming that the vast majority of patients require treatments of less than or equal to 30 minutes, a maximum total treatment time of 35 minutes would significantly inhibit the reuse of a single applicator to treat multiple patients. This treatment time is merely exemplary. The manufacturer could pre-set any maximum treatment time to help prevent applicator reuse without significantly decreasing the ease of proper use of the device. Additionally, the manufacturer could pre-set the maximum treatment time based on the types of patients and wounds typically encountered by a particular doctor, wound care clinic, or hospital. For example, users who treat patient populations with large, chronic wounds or with multiple wounds might have a device pre-set with a longer maximum treatment time to avoid exceeding the maximum treatment time during the treatment of a single patient.

By way of another example of means for preventing applicator reuse, the valve may include an expanding foam. The foam may slowly expand over time so that the foam eventually occludes the valve and blocks the flow of fluid from the bottle (or other fluid container) and through the valve to the transducer tip. Alternatively, the foam may expand very rapidly after a particular period of time. For example, the foam may expand very rapidly approximately 35 minutes after the foam is first contacted with fluid. A rapidly expanding foam may be preferable to prevent changes in fluid flow characteristics or drop size during the treatment time. Whether the foam is a slowly or rapidly expanding foam, the foam is substantially inert such that its presence in the valve does not contaminate the fluid.

Another exemplary means for preventing applicator reuse involves the use of a radio frequency tag (RFID tag). Using an RFID tag, the ultrasound wound therapy device can identify when an applicator is attached to the transducer assembly and whether the applicator had been previously used (e.g., previously attached to a transducer assembly). In one embodiment, an RFID tag may be placed on the applicator and an RFID tag reader may be placed on the transducer assembly. The reader is interconnected to a microprocessor in the ultrasound wound therapy device and is capable of reading the RFID tag in the applicator. In one embodiment, the reader is integrated into the control flow of the ultrasound wound therapy device such that identification of an RFID tag on an unused applicator by the reader is necessary before the transducer assembly can be activated (e.g., is necessary to use the device). Once the reader identifies the RFID tag and identifies that the applicator is attached to the transducer assembly, the reader can modify the RFID tag such that the applicator is marked as "used." If the applicator is detached from the transducer assembly, and an operator attempts to reattach the used applicator to the same or a different transducer assembly, the RFID tag reader will identify the applicator as used and will not allow activation of the transducer assembly. Thus, the RFID tag prevents detachment and reuse of an applicator.

Numerous RFID technologies exist, and the invention contemplates the use of various types of RFID tags. By way of example, the RFID tag may be a passive RFID tag. Passive RFID tags do not require a battery to operate and reflect data to the reader. Generally, when passive RFID tags are used, the reader (also known as a detector) pings the RFID tag (e.g., the tag on the applicator) at one frequency and detects a tone received at the same or at a different frequency. Passive RFID tags can be relatively simple, for example, the tag may be a coil with a capacitor forming a resonant circuit.

Another type of RFID tag that may be used in the devices of the present invention is a semi-active RFID tag. Semi-active RFID tags contain an internal battery that improves the strength of data transmission between the tag, in this case a tag on the applicator, and the reader, in this case a reader on the transducer assembly.

Yet another type of RFID tag suitable for use in the device of the present invention is an active RFID tag. An active RFID tag uses a battery to power both the receiver and the transmitter in the RFID tag. Active RFID tags permit the longest transmit range. Although such active tags may be used in the present devices, the additional transmit range achieved using this technology may be unnecessary given the relatively small distances between the applicator and transducer assembly.

Additionally, in any of the foregoing, RFID tags may be used to prevent activation of the transducer assembly until an applicator has been attached to the transducer assembly. In other words, prior to activation of the transducer assembly the system detects the presence of the applicator by reading the RFID tag on the applicator. If an applicator is not detected as attached to the transducer assembly, the transducer assembly cannot be activated. This mechanism may provide a safety feature. Given that the applicator's shape helps to shield the transducer tip, the applicator helps protect patients and device operators from inadvertent contact with the vibrating transducer tip. Thus, the use of an RFID tag or other mechanism that requires applicator attachment prior to activation of the transducer assembly provides an additional safety feature and helps ensure that patients and operators derive the full protective benefits of the applicator design.

The applicators of the present invention, as well as the ultrasound wound therapy devices and transducer apparatuses disclosed herein and in U.S. Pat. Nos. 6,569,099, 6,478,754 and 6,663,554, and U.S. patent application Ser. No. 09/684,044 allow for improved methods of wound care. Specifically, it has been shown that the devices outlined herein and in the previous applications can be successfully used to improve the treatment of wounds. The delivery of ultrasound energy and a fluid spray from a non-contact distance results in beneficial effects including, but not limited to, decreased healing time, improved healing (e.g., more complete wound closure), and decreased incidence of infection. Without being bound by theory, this may be due to the ability of the emitted ultrasound energy and/or the fluid spray to penetrate the wound tissue to a beneficial depth. Additionally, action of the ultrasonic energy and/or the fluid spray at the wound surface may contribute to the therapeutic effect.

Regardless of the particular mechanism by which the delivery of ultrasonic energy and a fluid spray at a non-contact distance improves wound healing and decreases infection, the results are astounding. Briefly, emitted energy and the fluid spray are applied to the wound for a treatment time proportional to the size of the wound. The approximate size of the wound is entered into the ultrasound wound therapy device and the device sets a treatment time based on the size of the wound. Generally, treatment times vary from approximately 5 minutes to approximately 30 minutes. However, shorter and longer treatment times are contemplated. Once emitted energy and fluid spray are emerging from the applicator, the operator can direct the energy and spray to the wound. In one recommended embodiment, the wound is treated by slowly moving the applicator head back and forth and/or up and down (at a non-contact distance) across the wound. The spray pattern may be, for example, serpentine or substantially checkerboard in pattern. This delivery method has two advantages. First, this method helps insure that ultrasonic energy and liquid spray are delivered to the entire wound. Second, this method may help prevent operator fatigue that would likely result if the device was held in substantially the same place throughout the treatment. In one embodiment, the applicator is held such that the ultrasonic energy and liquid spray are delivered substantially normal to the surface of the wound. Additionally, the spray pattern may include moving the applicator in-and-out relative to the wound surface (e.g., varying the distance from the wound while maintaining a non-contact distance). Such a spray pattern helps ensure that a wound, which varies in depth across its surface area, is treated at an effective distance.

In one embodiment, the need for a human operator is eliminated. The transducer assembly is affixed to a robotic arm programmed to direct the emitted energy and liquid spray to the wound.

As outlined above, in certain embodiments the emitted ultrasonic energy and fluid spray are applied to the wound for a treatment time proportional to the size of the wound. In one embodiment, the invention provides a treatment algorithm for selecting treatment time based on the size of the wound. The time for each treatment is selected based on the area of the wound. The area of the wound is calculated by measuring the length of the wound (at its greatest point) and the width of the wound (at its greatest point and perpendicular to the length). The length and width of the wound can be measured, for example, in centimeters. The area of the wound (in square centimeters) is calculated by multiplying the length times the width of the wound. The treatment time is proportional to the area of the wound.

Based on the algorithm, the following treatment times may be selected based on wound size: 3 minutes for wounds with an area of less that 10 cm$^2$; 4 minutes for wounds with an area of 10-20 cm$^2$; 5 minutes for wounds with an area of 20-30 cm$^2$; 6 minutes for wounds with an area of 30-40 cm$^2$; 7 minutes for wounds with an area of 40-50 cm$^2$; 8 minutes with an area of 50-60 cm$^2$; 9 minutes for wounds with an area of 60-70 cm$^2$; 10 minutes for wounds with an area of 70-80 cm$^2$; 11 minutes for wounds with an area of 80-90 cm$^2$; 12 minutes wounds with an area of 90-100 cm$^2$.

In certain embodiments, the ultrasonic wound therapy device is programmed with the algorithm. The operator enters the wound size into the device using a keypad. A treatment time is selected based on the wound size. In certain embodiments, the ultrasound wound therapy device includes a timer that counts down from the treatment time. When the treatment time has elapsed (e.g., the timer has ticked down to zero), the ultrasound wound therapy device may automatically shut off. In other words, after the treatment time has elapsed, the power shuts off and the transducer stops vibrating. It is appreciated that a timer and automatic shut off mechanism have utilities apart from their use in conjunction with treatment times proportional to wound size. Such timers may be used even in the absence of a treatment time algorithm (e.g., a timer can be used when the total treatment time is selected by the individual operator). Additionally or alternatively, an alarm may sound to alert the operator when the treatment time has elapsed.

The above algorithm does not direct the frequency of treatments. Furthermore, as the wound heals, the treatment time may be reassessed and recalculated in accordance with the decreasing size of the wound. Additionally, the above treatment algorithm is only one way to select an appropriate treatment time. Wounds may be treated for a longer or shorter period of time than that recommended based on the treatment algorithm.

The present invention contemplates a variety of kits. In one embodiment, a kit includes an applicator (e.g., a nozzle, a valve, and a cup) and a bottle sized and shaped to fit onto the cup. The kit may optionally include directions for use and/or one or more sterile swabs. The sterile swabs can be used to wipe, prior to or after use, one or more of: the bottle, all or a portion of the applicator, all or a portion of the transducer, all or a portion of the cup, the puncturing device, all or a portion of the ultrasound wound therapy device.

In certain embodiments, the bottle includes a sterile fluid suitable for use in the treatment of a wound. Any of the foregoing kits may be sterilized prior to packaging such that the contents of the kit are sterile. The kits can be marked to indicate that they are intended for use with a single patient.

In another embodiment, the kit does not include a cup portion. In such embodiments, the applicator includes a nozzle and a valve. These kits may be specifically intended for use in conjunction with a fluid bag. Optionally, this applicator (nozzle and valve) may be packaged with a fluid bag including a fluid, and with flexible tubing sized and shaped to interconnect the fluid bag to the valve of the applicator. These kits may optionally include directions for use and/or one or more sterile swabs.

It is to be understood that the foregoing description is merely a disclosure of particular embodiments and is in no way intended to limit the scope of the disclosure. All operative combinations of any of the foregoing aspects and embodiments are contemplated and are within the scope of the invention. Other possible modifications will be apparent to those skilled in the art and all modifications will be apparent to those in the art and all modifications are to be defined by the following claims.

We claim:

1. An applicator for use in treating a wound, the applicator comprising:
    a nozzle including a proximal portion, a distal opening and a valve interface, the proximal portion being engageable with a portion of an ultrasound wound therapy device, the distal opening allowing at least a portion of a transducer tip of the ultrasound wound therapy device to pass therethrough, the valve interface defining an axis therethrough;
    a valve comprising a valve opening, an upper portion and a lower portion, the upper and lower portion being rotatable with respect to each other, the lower portion being engageable with the valve interface of the nozzle, and the valve opening allowing fluid to flow therethrough and allowing fluid flow to be reversibly turned on and off; and
    a cup including an aperture, the aperture in fluid communication with at least the upper portion of the valve,
    whereby, fluid can flow through the aperture of the cup, through the valve and onto at least a portion of the transducer tip of the ultrasound wound therapy device in a manner that avoids aerosolization when contacting the transducer tip.

2. The applicator according to claim 1, wherein when the nozzle is engaged with said ultrasound wound therapy device, the fluid drips on a portion of the transducer tip that is proximal to the distal-most portion of the tip of the ultrasound wound therapy device.

3. The applicator according to claim 1, wherein the cup further comprises a puncturing device which is capable of puncturing a bottle inserted onto the cup.

4. The applicator according to claim 1, wherein the cup further comprises an alignment structure which facilitates positioning a bottle in the cup.

5. The applicator according to claim 1, wherein the cup further comprises at least one indent which enhances the fit of a bottle in the cup.

6. The applicator according to claim 1, wherein the cup further comprises at least one indent which damages a bottle when the bottle is removed from the cup.

7. The applicator according to claim 1, wherein the valve is removable from at least one of the nozzle and the cup.

8. The applicator according to claim 1, wherein the cup is rotatable with respect to the axis defined by the valve interface.

9. The applicator according to claim 1, wherein the nozzle further comprises a distal tip, the distal tip being the portion of the nozzle which extends farthest distally, at least a portion of a transducer tip of the ultrasound wound therapy device extends between the distal opening of the nozzle and the distal tip of the nozzle.

10. The applicator according to claim 1, wherein the diameter of the valve opening is in the range of about 0.027 inches to about 0.037 inches.

11. The applicator according to claim 1, wherein the diameter of the valve opening is in the range of about 0.031 inches to about 0.033 inches.

12. The applicator according to claim 1, wherein the diameter of the valve opening causes fluid that travels therethrough to have a diameter equal to about 60 µm.

13. The applicator according to claim 1, wherein when the nozzle is engaged with said ultrasound wound therapy device, fluid drips on a front face of the transducer tip of the ultrasound wound therapy device.

14. The applicator according to claim 1, further comprising an integrated circuit (IC) chip disposed on the applicator, wherein the IC chip communicates with the transducer assembly or ultrasound wound therapy device to limit the number of times the applicator can be used with a transducer assembly.

15. The applicator according to claim 1, wherein the applicator is designed for use with a single patient and wherein the applicator comprises means to prevent re-use of the applicator.

16. The applicator according to claim 1, wherein the nozzle further comprises at least one vent hole.

17. The applicator according to claim 1, wherein the nozzle further comprises a plurality of aligning slots which facilitate the alignment between the nozzle and a transducer assembly.

18. The applicator according to claim 1, wherein at least one of the nozzle, the valve and the cup are disposable.

19. The applicator according to claim 1, further comprising a bottle.

20. The applicator of claim 1, further comprising a radio frequency identification (RFID) tag disposed on the applicator, wherein the RFID tag communicates with an RFID tag reader to indicate the number of times the applicator has been used and thereby limit the number of times the applicator can be used with the transducer assembly.

21. The applicator according to claim 1, wherein the cup contains a single puncturing device.

22. The applicator according to claim 1, wherein the fluid flows via gravity feed.

23. The applicator according to claim 8, wherein rotating the cup adjusts the valve from a closed position, to at least a partially open position.

24. The applicator according to claim 8, wherein the cup is configured to be rotated by a switch on a transducer assembly.

25. The application of claim 15, wherein the valve further includes an expandable foam.

26. The applicator according to claim 16, wherein the cup contains a single puncturing device.

27. The applicator according to claim 16, wherein each of the one or more vent holes has a diameter of about 0.05 inches to about 0.20 inches.

28. The applicator according to claim 19, wherein the bottle is inserted onto the cup.

29. The applicator of claim 19, wherein the bottle includes a sterilized fluid.

30. A method for promoting wound healing comprising the steps of:

providing a transducer which emits ultrasonic energy;

providing an applicator comprising:

a nozzle including a proximal portion, a distal opening and a valve interface, the proximal portion being engageable with a portion of an ultrasound wound therapy device, the distal opening allowing at last a portion of a transducer tip of the ultrasound wound therapy device to pass therethrough, a valve comprising a valve opening, an upper portion and a lower portion, the upper and lower portion being rotatable with respect to each other, the lower portion being engageable with the valve interface of the nozzle, the upper portion being in fluid communication with a fluid source, and the valve opening allowing fluid to flow therethrough and allowing fluid flow to be reversibly turned on and off, and a cup including an aperture, the aperture in fluid communication with at least the upper portion of the valve; and activating the transducer to emit ultrasonic energy; and turning the cup to selectively allow fluid to flow from the fluid source through the valve opening towards a portion of the transducer; wherein, following contact of said portion of the transducer with said fluid and activation of the transducer, a spray having consistent particle size and velocity is generated, and wherein the emitted ultrasonic energy is delivered to the wound through the fluid spray at a non-contact distance of at least 0.1 inches from the wound.

31. The method according to claim 30, wherein when the transducer is activated, the transducer tip vibrates at a rate of about 1 kHz to about 10,000 MHz.

32. The method according to claim 30, wherein the fluid source is a bottle containing fluid.

33. The method according to claim 30, wherein the emitted ultrasonic energy and the fluid spray are delivered to the wound for a treatment time which is proportional to the size of the wound.

34. The method according to claim 30, wherein the emitted ultrasonic energy and the fluid spray are delivered to the wound by moving the applicator in a serpentine or checkerboard pattern relative to the wound.

35. The method according to claim 30, wherein the fluid source is a fluid bag.

36. The method of claim 30, wherein the step of turning the cup to selectively allow fluid to flow from the fluid source through the valve opening towards a portion of the transducer is performed before the step of activating the transducer.

37. The method of claim 30, wherein one or more vent holes are disposed on the nozzle.

38. The method of claim 30, wherein the cup contains a single puncturing device.

39. The method of claim 30, wherein the fluid is not pressurized.

40. The method according to claim 31, wherein the transducer tip vibrates at a rate of about 30 kHz to about 50 kHz.

41. A kit comprising, an applicator comprising:
a nozzle including a proximal portion, a distal opening and a valve interface, the proximal portion being engageable with a portion of an ultrasound wound therapy device, the distal opening allowing at least a portion of a transducer tip of the ultrasound wound therapy device to pass therethrough, the valve interface defining an axis therethrough,
a valve comprising a valve opening, an upper portion and a lower portion, the upper and lower portion being rotatable with respect to each other, the lower portion being engageable with the valve interface of the nozzle, and the valve opening allowing fluid to flow therethrough and allowing fluid flow to be reversibly turned on and off, and
a cup including an aperture, the aperture in communication with at least the upper portion of the valve; and
a bottle, wherein the bottle is not pressurized.

42. The kit according to claim 41, further comprising instructions for use and one or more sterile swabs for cleaning one or more of a surface of the bottle, a portion of the applicator, a puncturing device, or a portion of an ultrasound wound therapy device.

43. The kit according to claim 41, wherein the bottle includes a fluid and the fluid is sterilized.

44. The kit according to claim 41, wherein the cup further comprises a puncturing device which is capable of puncturing a bottle inserted onto the cup.

45. The kit according to claim 41, wherein the cup further comprises an alignment structure which facilitates positioning a bottle in the cup.

46. The kit according to claim 41, wherein the cup further comprises at least one indent which enhances the fit of a bottle in the cup.

47. The kit according to claim 41, wherein the cup further comprises at least one indent which damages a bottle when the bottle is removed from the cup.

48. The kit according to claim 41, wherein the applicator is designed for use with a single patient and wherein the applicator comprises means to prevent reuse of the applicator.

49. The kit according to claim 41, wherein the bottle includes a fluid and the fluid includes a therapeutic drug.

50. The kit according to claim 41, wherein the bottle includes a fluid and the fluid comprises saline.

51. The kit according to claim 41, wherein the bottle includes a fluid and the fluid consists of saline.

52. The kit according to claim 41, wherein the bottle includes a fluid and the fluid does not include a therapeutic drug.

53. The kit according to claim 42, wherein the kit is labeled as intended for use with a single patient.

54. The kit according to claim 44, further comprising instructions for use and one or more sterile swabs for cleaning one or more of a surface of the bottle, the cup portion of the applicator, the puncturing device, or a portion of an ultrasound wound therapy device.

55. The kit according to claim 50, wherein the bottle includes a fluid and the fluid does not include a therapeutic drug.

56. A kit comprising, an applicator comprising:
a nozzle including a proximal portion, a distal opening, and a valve interface, and at least one vent hole, the proximal portion being engageable with a portion of an ultrasound wound therapy device, the distal opening allowing at least a portion of a transducer tip of the ultrasound wound therapy device to pass therethrough, the valve interface defining an axis therethrough, and
a valve comprising a valve opening, an upper portion and a lower portion, the upper and lower portion being rotatable with respect to each other, the lower portion being engageable with the valve interface of the nozzle, and the valve opening allowing fluid to flow therethrough and allowing fluid flow to be reversibly turned on and off; and
a fluid bag.

57. The kit according to claim 56, further comprising instructions for use and one or more sterile swabs for cleaning one or more of a surface of the fluid bag, a portion of the applicator, or a portion of an ultrasound wound therapy device.

58. The kit of claim 56, wherein each of the one or more vent holes has a diameter of about 0.05 inches to about 0.20 inches.

59. The method of claim 37, wherein each of the one or more vent holes has a diameter of about 0.05 inches to about 0.20 inches.

* * * * *